United States Patent [19]

Seber

[11] Patent Number: 4,745,916

[45] Date of Patent: May 24, 1988

[54] SUN BLOCK AND GLARE REFLECTIVE TAPES AND PATCHES

[76] Inventor: Brett P. Seber, 25002 Adelanta Dr., Laguna Niguel, Calif. 92677

[21] Appl. No.: 14,701

[22] Filed: Feb. 13, 1987

[51] Int. Cl.$^4$ .............................................. A61F 13/00
[52] U.S. Cl. ..................................................... 128/155
[58] Field of Search ............... 128/155; 132/88.5, 88.7

[56] References Cited

U.S. PATENT DOCUMENTS

| | | | |
|---|---|---|---|
| 1,850,540 | 3/1932 | Erickson | 132/88.5 |
| 2,527,947 | 10/1950 | Loos | 132/88.5 |
| 2,851,805 | 9/1958 | Allen | 132/88.5 |
| 3,485,251 | 12/1969 | Brunet | 132/88.5 |
| 3,736,946 | 6/1973 | Yando | 132/88.5 |

*Primary Examiner*—Gregory E. McNeill
*Attorney, Agent, or Firm*—Philip D. Junkins

[57] ABSTRACT

Sun blocking and glare reflective and absorptive tapes and patches for applications to skin areas of human individuals to block, reflect, deflect or absorb sunlight or artificial light to protect sensitive skin areas and the eyes. The tape and patch materials are comprised of a thin non-woven, random-spun synthetic fiber textile material capable of blocking ultra-violet radiation and a skin-compatible, pressure sensitive, non-toxic, hypo-allergenic, non-irritating adhesive applied to the textile material for holding same to the skin surface to be protected or reflect or absorb light glare. The non-woven textile material has a print surface on the side of such material opposite to the side bearing the pressure sensitive adhesive. The tape and patch material is mounted, for pre-use purpose, i.e., printing, packaging and storage, on release paper. The pressure sensitive adhesive leaves no residue on the skin surface after removal of the tape or patch because the adhesive has greater cohesion to itself and adhesion to the textile material than its adhesion to skin surfaces.

7 Claims, 1 Drawing Sheet

SUN BLOCK AND GLARE REFLECTIVE TAPES AND PATCHES

BACKGROUND OF THE INVENTION

The present invention relates to sun block and glare reflective materials. More particularly, the invention relates to materials for providing sunburn protection for people engaged in activities involving high exposure to the sun and for providing glare reduction means for people engaged in activities involving exposure to uncomfortably bright lights.

Beach and pool swimmers and sun bathers, ocean surfboard riders, sail and power boat operators, football players, and even snow skiers, to name but a few, are exposed to high degrees of sun light and need sunburn protection from overexposure to sunlight. Numerous lotions, salves, ointments and other sunblocking materials have been proposed, and are in use, for protecting sun-sensitive skin areas of persons engaged in activities where sunlight exposure is desired, expected or required. Also, amateur and professional athletes of all types are exposed to sun glare or the uncomfortable effects of bright artificial lights. Such athletes frequently apply light reflecting or light absorbing materials, such as black theatrical grease paint or carbon black powder and the like, to skin areas (cheek bone areas) which normally reflect or deflect sunlight or artificial light into the athletes eyes. The various sunblocking materials and light reflecting and absorbing materials are often irritating to the skin areas to which they are applied and are frequently difficult to remove from such skin areas.

It is a principal object of the present invention to provide tape and patch materials which can be applied to sunsensitive skin areas of persons to protect such areas from the harmful effects of sunlight.

It is a further object of the invention to provide tape and patch materials which can be applied to skin areas of athletes to reflect, deflect or absorb sunlight or artificial light to protect the eyes of such athletes from harmful sun or artificial light glare.

It is a still further object of the invention to provide sun block protective and light glare reflective tape and patch materials which are non-toxic, hypo-allergenic and non-irritating to the skin areas to which they are applied.

It is yet another object of the invention to provide sun block protective and light glare reflective tape and patch materials which are attractive and stylish or fashionable.

SUMMARY OF THE INVENTION

The foregoing and other objects and advantages of the invention are attained in accordance with the present invention by providing sun blocking tapes and patches, and glare reflective tapes and patches, which are basically comprised of: a thin non-woven, random-spun synthetic fiber textile material capable of blocking ultra-violet radiation; and a skin-compatible, pressure sensitive, non-toxic, hypo-allergenic, non-irritating adhesive applied to such textile material for holding same to the skin surface of an individual desiring or requiring sun blocking or glare protection. The non-woven textile material has a print surface on the side of such material opposite to the side bearing the pressure sensitive adhesive. Prior to the application of a tape section or patch of the sun block or glare reflecting material of the invention, such tape section or patch is mounted on a release paper. The pressure sensitive adhesive leaves no residue on the skin surface after removal of the tape or patch because the preferred adhesives have greater cohesion to themselves and adhesion to the random-spun synthetic fiber textile materials, forming the tapes and patches, than its adhesion to the skin surface. Colorful designs or graphics and photographic images may be printed on the print surface of the sun blocking tapes and patches and glare reflective tapes and patches to make such tapes and patches items of fashion wear, as-well-as items having an important sun or glare protective function.

DETAILED DESCRIPTION OF THE INVENTION

Figure 1:
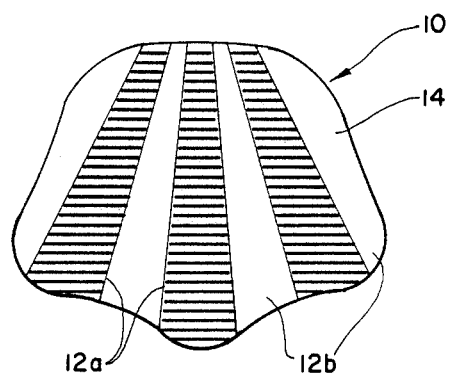
FIG. 1 is a top plan view of a sun block patch in accordance with the present invention, the patch being mounted on a release paper prior to its application to the nose area of an individual.
Figure 2:
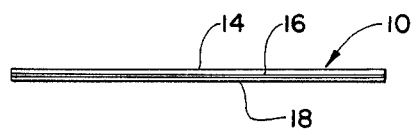
FIG. 2 is a front edge view of the sun block patch shown in FIG. 1.

Reference is now made to the drawing sheet. In FIGS. 1 and 2 there is shown an exemplary sun block patch 10 in accordance with the present invention. The particular sun block patch is configured to provide sun shield protection to the surfaces of the nose of an individual using such patch. In the plan view of FIG. 1 the patch 10 bears on its upper (outer) printable surface a fashion or style design comprising (as illustrated) color stripes 12a in contrast with background areas 12b which may be of skin or other color. The sun block patch 10 is comprised of: a layer 14 of non-woven, random-spun (or spunbonded) synthetic fiber fabric material capable of blocking harmful ultra-violet radiation; and a relatively thin layer 16 of skin-compatible, pressure sensitive, non-toxic, hypo-allergenic, non-irritating adhesive material applied to the underside of the non-woven material 14 by any one of many well-known methods. The sun block or sun shield patch 10 is mounted, for pre-use purposes (printing, packaging, storage, etc.), on release paper 18 of any well-known type (silicone release paper, wax paper, etc.).

The non-woven, synthetic fiber fabric material layer 14 of the sun block patch 10 may be formed of random-spun or spunbonded polyester and polyamide fibers and mixed polyamide/polyester fibers (fabric weight of $\frac{1}{4}$ to 2 oz/yd$^2$ and thickness of $\frac{1}{2}$ to 4 mils). Alternatively, such layer may comprise fabrics of spunlaced polyester fibers, polyester/rayon blend fibers and polyester/cellulosic blend fibers such as "SONTARA" brand polyester fabrics produced by E. I. DuPont de Nemours & Co. These latter materials (thickness range of 10–40 mils) are soft, strong, conformable and light weight (1–4 oz/yd$^2$), impervious and printable, and (with appropriate coloring) may present a skin-like appearance. Further, SONTARA fabrics exhibit good wet and dry strength and contain no chemical binders to irritate skin areas. Another DuPont fabric of interest as the non-woven, synthetic fiber material layer 14 of the sun block patch 10 of the present invention, is "DUROGRAF" brand spunbonded polyester fiber which has been coated with an acrylic emulsion to impart superior printing characteristics, i.e., high acceptability to silk screen printing inks. Typically DUROGRAF fabrics weigh about 3 oz/yd$^2$ and have a thickness of about 6 mils.

The skin-compatible, non-toxic, hypo-allergenic, non-irritating adhesive 16, applied to the underside of the non-woven fabric material 14 of the sun block or sun shield patch 10, may be a pressure sensitive aqueous based or solvent based adhesive formed of polymerized or copolymerized acrylic or vinyl polymer or a hot melt adhesive of acrylic based or rubber based type. Preferably, the adhesive 16 is an emulsion type (aqueous based) acrylic adhesive which leaves no residue on the skin surface after removal of the patch 10 because such adhesive has greater cohesion to itself and adhesion to the fabric material 14 than its adhesion to the skin surface. Because of the foregoing cohesion/adhesion characteristics of the adhesive 16, the sun block patch 10 of the invention may be reused, i.e., reapplied to skin surfaces a number of times.

Figure 3:
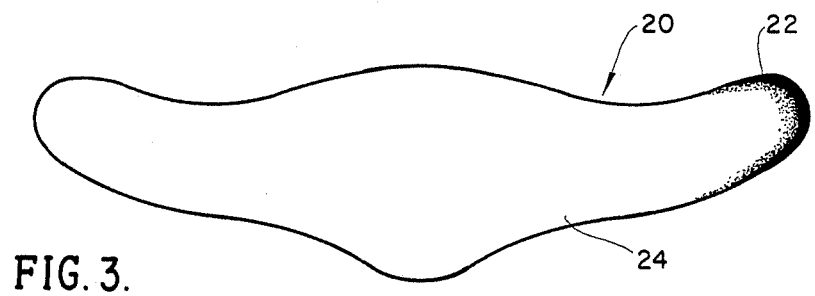
FIG. 3 is a top plan view of a glare reflecting tape in accordance with the present invention, the tape being mounted on a pressure release paper prior to its application to the nose and cheek bone areas of an individual.
Figure 4:
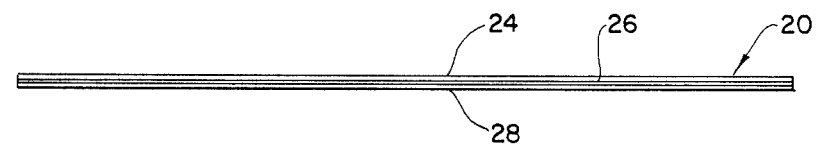
FIG. 4 is a front edge view of the glare reflecting tape shown in FIG. 3.

Referring now to FIGS. 3 and 4 there is shown an exemplary glare reflective or glare absorptive tape 20 in accordance with the invention. The particular reflective or absorptive tape is configured to provide glare reflection protection to the eyes of persons (particularly athletes) exposed to sun glare or the uncomfortable effects of bright artificial lights. The elongated tape 20 is designed to be applied over the bridge of the nose of the subject and extend across the cheek bone areas below the eyes of the subject. In the plan view of FIG. 3 the tape 20 bears on its upper (outer) printable surface a dark color area 22, preferably dull black, for absorbing light glare. The glare reflective or absorptive tape 20 is comprised of: a layer 24 of non-woven, random-spun (or spunbonded) synthetic fiber fabric material (of the type described with respect to material 14 of FIG. 1) capable of absorbing or reflecting harmful sun or artificial light glare; and a relatively thin layer 26 of skin-compatible, pressure sensitive, non-toxic, hypo-allergenic, non-irritating adhesive material 26 (of the type described with respect to adhesive 16 of FIG. 2). As shown in FIGS. 3 and 4, the glare reflective or glare absorptive tape 20 is mounted on release paper 28 of any well-known type.

The following examples include actual material and structural data respecting sun block and glare reflective or absorptive tape and patch materials in accordance with the embodiments of the invention.

EXAMPLE I

Sun block tape and patch material was fabricated in accordance with the invention. Commerically available non-woven fabric comprised of a blend of spunbonded polyester and cellulosic fibers, having a printable surface on one side thereof, was utilized as the principal tape and patch material. This synthetic fiber material had a uniform thickness of 4 mils and weighed 1 oz/yd$^2$. The side of the fabric opposite the printable side thereof was coated with emulsion based acrylic adhesive material (66% solids by volume). The acrylic adhesive emulsion was applied to the fabric in a quantity relationship of 3 gallons of emulsion for 1060 square feet of fabric. Following application of the adhesive the fabric was heated to remove water and then cooled to set the adhesive. The resulting non-toxic, hypoallergenic, pressure sensitive adhesive layer measured 2 mils in thickness. The fabricated sun block tape and patch material was thereafter adhered (for temporary mounting purpose) to a layer of silicone release paper and the printable surface of the composite material (fabric, pressure sensitive adhesive coating and release paper) was printed with appropriate fashion design graphics by silk screen methodology. Final sun block tape and patch configurations were die cut from the printed composite material and packaged as one product form of the invention. In use, various forms of the composite tape and patch material were removed from the release paper and applied to the skin areas of an individual exposed to bright beach sun light (including strong ultraviolet rays). The patch and tape material adhered well to the subject's skin areas, effectively blocked the areas from sun exposure, were attractive in appearance and did not loosen although the subject exposed the patches and tapes to considerable amounts of ocean salt water. After use, the sun block patches and tapes were removed and replaced on the release paper for future repeated use. No residual adhesive appeared on the skin areas covered by the patches and tapes and such areas showed no signs of skin irritation from the patches and tapes.

EXAMPLE II

Sun glare absorptive tape material was fabricated in accordance with the invention. Commercially available "DUROGRAF" brand spunbonded (non-woven) polyester fabric (manufactured by DuPont), coated on one side with an acrylic emulsion to impart exceptional printing characteristics for standard silk screen printing inks, was utilized as the principal tape material. This synthetic fiber material, as used, had a uniform thickness of 6 mils, weighed 3.1 oz/yd$^2$, and exhibited excellent resistance to ultraviolet radiation. The material is unaffected by moisture and is of uniform opacity. The side of the fabric opposite the printable side thereof was coated with emulsion based acrylic adhesive material (66% solids by volume). The acrylic adhesive emulsion was applied to the fabric in a quantity relationship of 4 gallons of emulsion for 1060 square feet of fabric. Following application of the adhesive material the fabric was heated to remove water and then cooled to set the adhesive. The resulting pressure sensitive adhesive layer measured 2.3 mils in thickness. The fabricated sun glare tape material was thereafter adhered (for temporary mounting purpose) to a layer of silicone release paper and the printable surface of the composite material (fabric, pressure sensitive adhesive coating and release paper) was printed with a dull black ink by silk screen methodology. Final sun glare absorptive tape configurations were die cut from the printed composite material and packaged as a product form of the invention for protecting the eyes of athletes from harmful sun glare such as experienced by football players or competitive snow skiers. In use, various forms of the composite tape material were removed from the release paper and applied to the skin areas over the nose and under the eyes (across the cheek bones) of a skier exposed to bright direct sun light and sun light reflected from snow surfaces. The tape material adhered well to the skier's skin areas under the eyes, effectively absorbed direct and indirect sun radiation so that it did not reflect from the cheek bone areas into the eyes and the tape material did not loosen although subjected to considerable body moisture and snow. After use, the sun glare tape material was removed and replaced on the release paper for future use. No residual adhesive material appeared on the skin areas covered by the tape and such areas showed no sign of skin irritation as a result of use of the tape.

While the invention has been described in detail and with reference to specific embodiments thereof, it will be apparent to one skilled in the art that various changes and modifications can be made therein without departing from the spirit and scope of the invention as expressed in the following claims.

What is claimed is:

1. Composite tape and patch materials for applying to skin areas of human individuals to block harmful sun exposure and provide glare protection comprised of:
   (a) a layer of flexible non-woven fabric material formed of random-spun or spunbonded synthetic fibers selected from the group consisting of polyester fibers, polyamide fibers, blends of polyester and polyamide fibers and blends of polyester or polyamide fibers and cellulosic fibers, said non-woven fabric material being capable of blocking harmful ultra-violet radiation and having a printable surface on one side thereof for receiving printed designs, graphics and photographs; and
   (b) a relatively thin adhesive coating on the side of said non-woven fabric material opposite the side of said fabric material having a printable surface thereon, said adhesive coating being skin-compatible, non-toxic, hypo-allergenic and non-irritating and selected from the group consisting of emulsion based, solvent based and hot melt type adhesives, and said adhesive being pressure sensitive having greater cohesion to itself and adhesion to said non-woven fabric material than its adhesion to a skin surface.

2. The composite tape and patch materials for applying to skin areas of human individuals to block harmful sun exposure and provide glare protection as claimed in claim 1 wherein the layer of flexible non-woven fabric material weighs between 1 and 4 oz/yd$^2$, has a thickness of from 3 to 10 mils and is opaque.

3. The composite tape and patch materials for applying to skin areas of human individuals to block harmful sun exposure and provide glare protection as claimed in claim 1 wherein the emulsion based, solvent based or hot melt type adhesive is selected from the group comprising rubber, acrylic and vinyl polymers and copolymers.

4. The composite tape and patch materials for applying to skin areas of human individuals to block harmful sun exposure and provide glare protection as claimed in claim 1 wherein said material is initially mounted on a release paper.

5. The composite tape and patch materials for applying to skin areas of human individuals to block harmful sun exposure and provide glare protection as claimed in claim 1 wherein the printable surface of the flexible non-woven fabric material is imprinted with a light absorptive color.

6. The composite tape and patch materials for applying to skin areas of human individuals to block harmful sun exposure and provide glare protection as claimed in claim 1 wherein the adhesive coating on said fabric material is capable of blocking harmful ultra-violet radiation.

7. The composite tape and patch materials for applying to skin areas of human individuals to block harmful sun exposure and provide glare protection as claimed in claim 1 wherein the printable surface on said non-woven fabric material is imprinted with color fashion designs which at least in part act as a light absoptive medium.

* * * * *